United States Patent [19]  
Wu et al.

[11] 4,282,384
[45] * Aug. 4, 1981

[54] PREPARATION OF DIISOPROPYLEBENZENE HYDROPEROXIDE

[75] Inventors: Ching-Yong Wu, Fox Chapel Borough; Harold E. Swift, Gibsonia; John E. Bozik, Plum Borough, all of Pa.

[73] Assignee: Gulf Research & Development Company, Pittsburgh, Pa.

[*] Notice: The portion of the term of this patent subsequent to May 8, 1996, has been disclaimed.

[21] Appl. No.: 146,232

[22] Filed: May 5, 1980

[51] Int. Cl.$^3$ .......................................... C07C 179/035
[52] U.S. Cl. ................................................... 568/574

[58] Field of Search .................................. 568/574, 575

[56] References Cited

U.S. PATENT DOCUMENTS

| 2,632,774 | 3/1953 | Conner et al. | 568/574 |
| 4,153,635 | 5/1979 | Wu et al. | 568/574 |

*Primary Examiner*—Werren B. Lone
*Attorney, Agent, or Firm*—Deane E. Keith; Forrest D. Stine; Donald L. Rose

[57] ABSTRACT

The hydroperoxides of diisopropylbenzene are prepared by the oxidation of diisopropylbenzene with molecular oxygen in the presence of a minute amount of solid barium oxide.

11 Claims, No Drawings

PREPARATION OF DIISOPROPYLBENZENE HYDROPEROXIDE

SUMMARY OF THE INVENTION

This invention relates to an anhydrous process for the preparation of the mono- and dihydroperoxides of diisopropylbenzene by oxidation using molecular oxygen in the presence of a catalyst comprising a minute amount of solid barium oxide.

DESCRIPTION OF THE PRIOR ART

U.S. Pat. No. 2,632,774 describes the preparation of cumene hydroperoxide from cumene by oxidation of the cumene with molecular oxygen in the presence of one percent and two percent calcium hydroxide. The oxidation of p-diisopropylbenzene is also mentioned. Other alkali metal and alkaline earth metal compounds, including barium oxide, are listed with the amount used being dependent on the basic compound actually used. However, this patent specifies time and temperature as the critical variables, both of which are related by an expressed formula.

DESCRIPTION OF THE INVENTION

As described in our U.S. Pat. No. 4,153,635, we have discovered that a minute amount of barium oxide catalyzes the oxidation of cumene with molecular oxygen at substantially maximum reaction rate to cumene hydroperoxide. We have also shown in that patent that the presence of a large amount of barium oxide, although it increases the rate of cumene oxidation over that resulting with no barium oxide present, produces larger quantities of undesirable by-products and surprisingly lowers the rate of cumene oxidation over that resulting with a minute amount of barium oxide. We have now determined that a minute amount of barium oxide also increases the rate of oxidation of diisopropylbenzene while a larger amount actually decreases the rate over that resulting from oxidation in the absence of barium oxide.

Alkyl-substituted aromatic hydrocarbons having a hydrogen atom on a tertiary carbon atom, such as cumene and diisopropylbenzene, are relatively easy to oxidize to the hydroperoxide by direct oxidation using molecular oxygen. The resulting hydroperoxide or dihydroperoxide can then be decomposed using known procedures to form a phenol or a diphenol as the case may be. Thus, phenol can be prepared from cumene while catechol, resorcinol and hydroquinone are respectively prepared from o-, m- and p-diisopropylbenzene.

A significant problem associated with the oxidation of these alkyl-substituted aromatic hydrocarbons to form the hydroperoxide or dihydroperoxide is the production of undesirable by-products, including vinyl-, carbonyl- and alcohol-substituted aromatic compounds. The presence of the vinyl-substituted derivative in the hydroperoxide product is especially undesirable when the hydroperoxide is decomposed to produce the phenolic derivative. In this decomposition reaction the vinyl compound will form various tar-like oligomers which end up as difficult to remove impurities in the desired phenolic product.

By our invention we have unexpectedly discovered that the maximum rate of oxidation of the diisopropylbenzene can be induced when a minute amount of barium oxide, that is an amount up to about 0.1 weight percent, is present during the oxidation reaction. It is highly unexpected that barium oxide is a superior catalyst for the desired reaction in these minute amounts. Furthermore, this is particularly unexpected because in larger amounts the barium oxide not only substantially decreases the oxidation rate of the diisopropylbenzene below the rate which occurs in the absence of barium oxide, but also catalyzes the decomposition of the small amount of the hydroperoxide that is produced.

In our procedure for preparing cumene hydroperoxide with barium oxide catalyst, the barium oxide is preferably introduced into the reactor as a finely divided powder in order to accelerate its dispersion throughout the liquid and hasten its availability as a catalyst. Therefore, it is preferred that the initial particle size be small enough to stay in suspension in the liquid phase. However, larger sized particles of barium oxide even including pellet size can be used since the stirring or agitation of the reactor contents will gradually break down and disperse the barium oxide, including this larger sized barium oxide, throughout the solution. Therefore, the initial particle size of the barium oxide can broadly range from about 20 microns to about 5 millimeters in diameter and preferably a particle size ranging between about 50 and about 1,000 microns is used.

When the solution containing the powdered barium oxide is heated up under agitation, a fairly rapid, distinct change in appearance occurs at about 80° C. This change can be described as a transition from a powdery appearance to a milky appearance. This transition to a milky solution is concomitant with the oxidation reaction, indicative of some type of interaction, probably physical, between the barium oxide and the organic phase to form a more intimate association. We believe that this transition is related to the unexpected catalytic effect exhibited by barium oxide. The experimental data suggests to us that a minute amount of the barium oxide is involved in this transition and that it is this barium oxide that is responsible for the positive catalytic effect and the concomitant increased selectivity. The experimental data further suggests that the excess of barium oxide above this minute amount is not involved in this transition but remains in solid particulate form and that it is this solid barium oxide that is responsible for the lowered selectivity.

This transition to a milky solution upon heating this organic solution containing dispersed barium oxide and these catalytic effects are believed to be unique with barium oxide since they are not observed with conventional bases, such as solid sodium hydroxide. When the stirring of this milky solution is stopped while the elevated temperature is maintained, the solution retains its milky appearance. When the unstirred solution is cooled to room temperature, it reverts to its powdery appearance and the barium oxide precipitates out, resulting in a clear solution. The oxidation reaction is carried out under anhydrous conditions since the presence of water results in lowered selectivity as well as a reduced rate of oxidation.

In order to obtain beneficial results in accordance with our invention, a minute amount of barium oxide is used for the oxidation of the diisopropylbenzene. Significant improvement in the oxidation rate of the diisopropylbenzene to the hydroperoxide results when barium oxide is used in an amount as low as about 0.0005 weight percent based on the diisopropylbenzene, but we prefer that at least about 0.001 percent barium oxide be used for a more significant improvement and we most prefer that at least about 0.002 percent be used. The maximum amount of barium oxide to obtain the desired catalytic effect of this invention should not exceed about 0.1 weight percent although higher amounts can be used, if desired, at appropriate conditions and with less than optimum results. We prefer that the maximum amount of barium oxide does not exceed about 0.025 weight percent and most prefer that it not exceed about 0.015.

Our process can be used in the oxidation of o-, m- or p-diisopropylbenzene or mixtures of any two or all three of these compounds. The preferred reactant is a substantially pure composition of one of the diisopropylbenzenes with the meta or para isomers being preferred over the ortho isomer because of the relatively lesser availability of the latter as well as the lesser utility of its resulting dihydric phenol.

In the oxidation of the diisopropylbenzene both the reaction rate and the product stability are a function of temperature. The temperature of the reaction solution can be as low as about 70° C., but we prefer that it be at least about 80° C. for a suitable rate of reaction. The maximum temperature should not exceed about 130° C. because of the greatly increasing instability of the hydroperoxide product at the higher temperatures, but we prefer that the reaction temperature not exceed about 100° C. for better control of this decomposition.

The oxidation of the diisopropylbenzene by our procedure can conveniently be carried out at an appropriate elevated pressure using any suitable source of molecular oxygen, such as air or pure oxygen, as the oxidizer. When the oxygen is mixed with diluent gas, it is important that the diluent be free of any reactive contaminant gas, such as a nitrogen oxide or an oxide of sulfur, which would adversely react with one or more of the components in the reaction vessel. Although the partial pressure of oxygen in the reaction vessel is not critical, we prefer that this partial pressure be at least about 10 psia (68.9 kPa) but a partial pressure of oxygen as low as about 5 psia (34.5 kPa) is useful. The partial pressure of oxygen can be as high as about 200 psia (1,376 kPa) or even higher, but we prefer that the partial pressure be no greater than about 50 psia (345 kPa).

It is desirable that a minor amount of a hydrocarbon hydroperoxide be initially present in the reactor to eliminate the substantial induction time required to initiate the oxidation reaction. This hydroperoxide initiator substantially increases the rate of oxidation in the early phase of the oxidation reaction. This initiator is desirably used in an amount up to about 5 weight percent based on the diisopropylbenzene used. Higher amounts can be present but do not exert an additional beneficial effect. It is preferred to use at least about 0.5 weight percent of the initiator hydroperoxide. Most preferably the hydroperoxide initiator is the same hydroperoxide that is produced in the reaction, however, any suitable hydrocarbon hydroperoxide can be used including both aromatic and paraffinic hydroperoxides. Other suitable hydroperoxide initiators include cumene hydroperoxide, ethylbenzene hydroperoxide, isobutane hydroperoxide, isopentane hydroperoxide, and the like.

Since diisopropylbenzene has two groups subject to hydroperoxidation, the reaction takes place in two steps. In the first step the diisopropylbenzene oxidizes to the monohydroperoxide and in the second step the monohydroperoxide oxidizes to the dihydroperoxide. As a practical matter, the overall oxidation reaction of all of the diisopropylbenzene to dihydroperoxide cannot be carried out to completion in one stage because the decomposition rate of the hydroperoxide moiety increases significantly as its concentration increases. This decomposition of the hydroperoxide results in a decrease in the selectivity of the reaction and an increase in the production of the undesired by-products. In order to minimize this decomposition the diisopropylbenzene is only partially oxidized in one stage, for example, between about 10 and about 60 percent and more desirably between about 20 and about 40 percent of the diisopropylbenzene. The product of this partial hydroperoxidation reaction is a mixture of the mono- and dihydroperoxides, with the monohydroperoxide derivative predominating, and the unreacted diisopropylbenzene.

The peroxidation reaction can be carried out as a batch reaction either in two separate reactors or, if one so chooses, in a single batch reactor. When two reactors are used, the diisopropylbenzene is oxidized in the first reactor at appropriate conditions and in the presence of barium oxide until the desired proportion of the diisopropylbenzene has been oxidized to a mixture containing unreacted diisopropylbenzene, the monohydroperoxide and the dihydroperoxide. In this first stage, the reaction is carried out until the reaction liquid contains between about 10 and about 60 mol percent hydroperoxide determined as monohydroperoxide, and preferably between about 20 and about 40 mol percent hydroperoxide.

After removing either the diisopropylbenzene, the dihydroperoxide or both from the first stage product mixture in this simple batch reaction, the remaining portion containing the monohydroperoxide is charged to the second batch reactor for further oxidation at appropriate conditions and also in the presence of barium oxide. An inert solvent, such as benzene, n-heptane and the like, in an amount up to about 80 weight percent can be used in this second stage oxidation, if desired, to reduce the hydroperoxide concentration in the reactor and thereby reduce its rate of decomposition.

If a single batch reactor is used, a repetitive-type batch processing system can be used. In this technique a mixture of unreacted diisopropylbenzene and the monohydroperoxide resulting from the preceding batch after the removal of the dihydroperoxide, together with make-up diisopropylbenzene to replace the amount oxidized in the preceding batch, is charged to the reactor and is oxidized at appropriate conditions in the presence of barium oxide. This operation is then repeated as many times as is desired.

A continuous reaction procedure can also be utilized whether in a continuous flow-through tube reactor, also called a continuous batch-type reaction, or in a continuous flow-through tank reactor. The monohydroperoxide in the reaction product can be further oxidized in either of these continuous techniques in another reactor in the same general manner as described above with respect to the simple batch reaction. Or the reaction product can be continuously recycled and fed to the reactor with make-up diisopropylbenzene after the product dihydroperoxide has been removed.

In all of these procedures, whether continuous or batch, the partial oxidation of the diisopropylbenzene is carried out in the presence of barium oxide at the conditions of temperature and pressure as described, until the reaction product contains between about 10 to 60 mol percent, preferably about 20 to 40 mol percent hydroperoxide determined as monohydroperoxide. The time of reaction is not critical but rather depends upon the temperature, pressure and other conditions utilized to produce the desired product composition. An inert solvent is generally not necessary but can be utilized, if desired, to reduce the hydroperoxide concentration.

DESCRIPTION OF PREFERRED EMBODIMENTS

In the following examples the diisopropylbenzene contained no reactive impurities and a maximum of 1.0 weight percent inert hydrocarbon isomers. The barium oxide, BaO, was 97.5 percent pure with barium carbonate and strontium oxide comprising the major impurities and was used as a 60-80 mesh powder. The air was dried to remove water and treated to remove carbon dioxide. Glass reactors equipped with stirrer, gas bubbling tube, sidearm fritted tube for removing sample and heating jacket were used for these experiments.

EXAMPLE 1

In a 300 ml glass reactor equipped with a stirrer, a gas bubbling tube and a side tube for removing liquid sample, are placed 150 ml (128 g) of m-diisopropylbenzene and 5 ml (5 g) of 70 percent t-butylhydroperoxide as an initiator. No barium oxide is used in this experiment. The stirrer was started and the reactor was heated up and maintained at 80° C. as air was bubbled through the reaction liquid for 12 hours at a rate of 100 ml per minute and at a pressure of 140 psi. At two-hour intervals, a one ml sample was removed from the reactor and analyzed by gas liquid chromatography, which gives the amount of the m-diisopropylbenzene, and by iodometric titration, which gives the total amount of hydroperoxide present in the reactor. Since the reaction product contains both m-diisopropylbenzene monohydroperoxide and m-diisopropylbenzene dihydroperoxide, the total amount of hydroperoxide on a molar basis as determined by iodometric titration would be expected to be greater than the molar amount of m-diisopropylbenzene that is found to be consumed. When less hydroperoxide is found than the diisopropylbenzene that is consumed, it is an indication that substantial non-selective decomposition is taking place. The results are set out in Table I showing the mol percent of m-diisopropylbenzene (DiPB) reacted and the total hydroperoxide as monohydroperoxide in mol percent.

TABLE I

| Hours | 2 | 4 | 6 | 8 | 10 | 12 |
|---|---|---|---|---|---|---|
| m-DiPD reacted | 3.05 | 6.07 | 9.15 | 10.11 | 14.50 | 18.55 |
| Monohydroperoxide | 3.66 | 6.17 | 9.02 | 12.47 | 16.00 | 19.87 |

EXAMPLE 2

Example 1 was repeated except that 0.005 g of barium oxide (0.0038 weight percent) was additionally present in the reactor. The results are set out in Table II.

TABLE II

| Hours | 2 | 4 | 6 | 8 | 10 | 12 |
|---|---|---|---|---|---|---|
| m-DiPB reacted | 2.29 | 6.56 | 11.30 | 17.67 | 24.94 | 30.02 |
| Monohydroperoxide | 3.41 | 7.96 | 14.14 | 20.82 | 28.35 | 35.45 |

EXAMPLE 3

Example 1 was repeated except that 0.01 g of barium oxide (0.0075 weight percent) was also present in the reactor. The results are set out in Table III.

TABLE III

| Hours | 2 | 4 | 6 | 8 | 10 | 12 |
|---|---|---|---|---|---|---|
| m-DiPB reacted | 3.30 | 8.83 | 12.92 | 18.44 | 23.68 | 29.50 |
| Monohydroperoxide | 4.71 | 9.82 | 14.72 | 20.95 | 26.23 | 32.14 |

EXAMPLE 4

Example 1 was repeated except that 0.04 g of barium oxide (0.03 weight percent) was also added to the reactor. The results are set out in Table IV.

TABLE IV

| Hours | 2 | 4 | 6 | 8 | 10 | 12 |
|---|---|---|---|---|---|---|
| m-DiPB reacted | 3.84 | 5.21 | 7.19 | 6.84 | 7.28 | 7.82 |
| Monohydroperoxide | 2.51 | 3.50 | 3.90 | 3.95 | 4.00 | 4.01 |

This experiment suggests that too much barium oxide slows down the oxidation of the m-diisopropylbenzene and speeds up the decomposition of the little hydroperoxide that is produced.

EXAMPLE 5

Into a 500 ml glass reactor are charged 292 ml (250 g) of p-diisopropylbenzene and 10 ml (10 g) of 70 percent t-butylhydroperoxide as an initiator. No barium oxide was present during the oxidation reaction. The solution was heated to 80° C. and air was bubbled through for 12 hours at the rate of 200 ml per minute and at a pressure of 140 psi. A one milliliter sample was removed every two hours for analysis. The results are shown in Table V.

TABLE V

| Hours | 2 | 4 | 6 | 8 | 10 | 12 | 14 |
|---|---|---|---|---|---|---|---|
| p-DiPB reacted | 0.72 | 1.66 | 3.54 | 5.43 | 7.51 | 9.65 | 11.90 |
| Monohydroperoxide | 1.34 | 3.09 | 5.10 | 7.59 | 10.26 | 12.24 | 14.93 |

EXAMPLE 6

Example 5 was repeated except that 0.015 g of barium oxide (0.006 weight percent) was also present in the reactor. The results are set out in Table VI.

TABLE VI

| Hours | 2 | 4 | 6 | 8 | 10 | 12 | 14 |
|---|---|---|---|---|---|---|---|
| p-DiPB reacted | 1.12 | 3.67 | 8.15 | 12.82 | 17.75 | 22.70 | 27.46 |
| Monohydroperoxide | 1.71 | 6.75 | 10.96 | 16.97 | 21.40 | 27.15 | 31.48 |

Even though the oxidation of diisopropylbenzene to the hydroperoxides of diisopropylbenzene in the presence of barium oxide is carried out under substantially anhydrous conditions preferably including the use of dried air and predried diisopropylbenzene, it is recognized that very low concentrations of water will result together with the small amount of by-products. It is believed that most of this water of reaction leaves the system but some of this water of reaction may react with the barium oxide to form a minor amount of barium hydroxide. Since barium hydroxide is an inferior catalyst for the oxidation reaction, the presence of water results in a reduced reaction rate and a lower selectivity. Advantageously, the present procedure of using a minute amount of barium oxide results in less by-product water and therefore less of the inferior barium hydroxide in the reactor. As used herein, the expression "substantially anhydrous barium oxide" contemplates barium hydroxide as a possible minor component, while "substantially anhydrous conditions" refers to the substantial absence of free water.

It is to be understood that the above disclosure is by way of specific example and that numerous modifications and variations are available to those of ordinary skill in the art without departing from the true spirit and scope of the invention.

We claim:

1. A process for oxidizing diisopropylbenzene to a mixture of mono- and diisopropylbenzene hydroperoxide comprising heating o-diisopropylbenzene, m-diisopropylbenzene, p-diisopropylbenzene or a mixture thereof in contact with about 0.0005 to about 0.1 weight percent barium oxide at a temperature between about 70° C. and about 130° C. under substantially anhydrous conditions and contacting said diisopropylbenzene with molecular oxygen.

2. A process for oxidizing diisopropylbenzene to a mixture of mono- and diisopropylbenzene hydroperoxide in accordance with claim 1 in which the oxidation reaction is carried out in the presence of between about 0.001 percent and about 0.025 weight percent barium oxide.

3. A process for oxidizing diisopropylbenzene to a mixture of mono- and diisopropylbenzene hydroperoxide in accordance with claim 1 in which the partial pressure of oxygen is between about 5 and about 200 psia.

4. A process for oxidizing diisopropylbenzene to a mixture of mono- and diisopropylbenzene hydroperoxide in accordance with claim 1 in which the oxidation reaction is carried out until the reaction solution contains between about 10 and about 60 mol percent hydroperoxide determined as monohydroperoxide.

5. A process for oxidizing diisopropylbenzene to a mixture of mono- and diisopropylbenzene hydroperoxide in accordance with claim 1 in which the diisopropylbenzene is m-diisopropylbenzene.

6. A process for oxidizing diisopropylbenzene to a mixture of mono- and diisopropylbenzene hydroperoxide in accordance with claim 1 in which the oxidation reaction is carried out in the presence of between about 0.002 percent and about 0.015 weight percent barium oxide.

7. A process for oxidizing diisopropylbenzene to a mixture of mono- and diisopropylbenzene hydroperoxide in accordance with claim 1 in which the diisopropylbenzene is p-diisopropylbenzene.

8. A process for oxidizing diisopropylbenzene to a mixture of mono- and diisopropylbenzene hydroperoxide in accordance with claim 1 in which the temperature is between about 80° C. and about 100° C.

9. A process for oxidizing diisopropylbenzene to a mixture of mono- and diisopropylbenzene hydroperoxide in accordance with claim 1 in which the partial pressure of oxygen is between about 10 and about 50 psia.

10. A process for oxidizing diisopropylbenzene to a mixture of mono- and diisopropylbenzene hydroperoxide in accordance with claim 1 in which the oxidation reaction is carried out until the reaction solution contains between about 20 and about 40 mol percent hydroperoxide determined as monohydroperoxide.

11. A process for oxidizing diisopropylbenzene to a mixture of mono- and diisopropylbenzene hydroperoxide in accordance with claim 1 in which the diisopropylbenzene is contacted with air.

* * * * *